United States Patent
Greene et al.

(10) Patent No.: US 7,361,464 B2
(45) Date of Patent: *Apr. 22, 2008

(54) METHOD, SYSTEMS AND KITS FOR IMMUNO-DETECTION OF EPITOPES EXPRESSED ON MOLECULES

(75) Inventors: Mark I. Greene, Penn Valley, PA (US); James Eberwine, Philadelphia, PA (US); Janet Estee Kacharmina, Davis, CA (US); Hongtao Zhang, Paoli, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/856,057

(22) Filed: May 28, 2004

(65) Prior Publication Data

US 2005/0003413 A1    Jan. 6, 2005

Related U.S. Application Data

(63) Continuation of application No. 09/624,946, filed on Jul. 25, 2000, now Pat. No. 6,743,592.

(51) Int. Cl.
*C12Q 1/68* (2006.01)
*C12P 19/34* (2006.01)

(52) U.S. Cl. .......................... 435/6; 435/91.1
(58) Field of Classification Search ............... 435/6, 435/91.2, 91.52, 7.1
See application file for complete search history.

(56) References Cited

U.S. PATENT DOCUMENTS

| | | | |
|---|---|---|---|
| 4,965,205 A | 10/1990 | Quentin-Millet et al. | |
| 5,334,702 A | 8/1994 | Greene et al. | 530/323 |
| 5,436,134 A | 7/1995 | Haughland et al. | 435/34 |
| 5,627,027 A | 5/1997 | Waggoner | |
| 5,631,129 A | 5/1997 | Chu et al. | |
| 5,663,144 A | 9/1997 | Greene et al. | 514/14 |
| 5,665,539 A | 9/1997 | Sano et al. | 435/6 |
| 5,874,226 A | 2/1999 | Zeytinoglu et al. | |
| 5,888,729 A | 3/1999 | Kacian et al. | |
| 5,919,764 A | 7/1999 | Greene et al. | 514/14 |
| 5,922,553 A | 7/1999 | Eberwine et al. | 435/7.92 |
| 5,985,548 A | 11/1999 | Collier et al. | |
| 6,022,523 A | 2/2000 | DeGrado et al. | 424/1.69 |
| 6,132,997 A | 10/2000 | Shannon | |
| 6,140,471 A | 10/2000 | Johnson et al. | |
| 6,172,197 B1 | 1/2001 | McCafferty et al. | |
| 6,225,447 B1 | 5/2001 | Winter et al. | |
| 6,248,527 B1 | 6/2001 | Chen et al. | |
| 6,291,650 B1 | 9/2001 | Winter et al. | |
| 6,743,592 B1 | 6/2004 | Greene et al. | |
| 7,045,286 B2 | 5/2006 | Greene et al. | |

FOREIGN PATENT DOCUMENTS

| | | |
|---|---|---|
| EP | 0544212 | 6/1993 |
| WO | WO94/26932 | 11/1994 |
| WO | WO98/22624 | 5/1998 |

OTHER PUBLICATIONS

Jones et al., "RNA quantitation by fluorescence-based solution assay: RiboGreen reagent characterization," *Analytical Biochemistry* (1998) 265(2):368-374.

Niemeyer et al., "Fluorometric polymerase chain reaction (PCR) enzyme-linked immunosorbent assay for quantification of immuno-PCR products in microplates," *Analytical Biochemistry* (1997) 246(1):140-145.

Ren et al, "Detection of circulating gastric carcinoma-associated antigen MG7-Ag in human sera using an established single determinant immuno-polymerase chain reaction technique," *Cancer* (2000) 88(2):280-285.

Murali et al., "Structure-based design of immunologically active therapeutic peptides," *Immunol Res* (1988) 17:163-169.

Saragovi et al., "Design and synthesis of a mimetic from an antibody complementarity-determining region," *Science* (1991) 253(5021):792-795.

Williams et al., "Development of biologically active peptides based on antibody structure," *Proc Natl Acad Sci USA* (1989) 86(14):5537-5541.

Zhang, et al., "Shared antigenic epitopes and pathobiological functions of anti-p185 her2/neu monoclonal antibodies," *Exp. Mol. Pathol.* (1999) 67:15-25.

Peterson and Greene, "Bacterial expression and characterization of recombinant biologically active anti-tyrosine kinase receptor antibody forms," *DNA Cell Biol.* (1998) 17:1031-1040.

Muller, et al., "Recombinant single-chain Fv antibody fragment-alkaline phosphatase conjugate for one-step immunodetection in molecular hybridization," *J. Immunol. Met.* (1999) 227:177-185.

Muller, et al., "Expression and functional characterization of a pHis-tagged human bradykinin B2 receptor in COS-7 cells," *Biol. Chem. Gremany* (2000) 381:343-347.

Monnet, et al., "Synthetic peptides derived from the variable regions of an anti-CD4 monoclonal antibody bind to CD4 and inhibit HIV-1 promoter activation in virus-infected cells," *J. Biol. Chem.* (1999) 274:3789-3796.

Felix, A.M., "Applications of BOP reagent in solid phase synthesis", *Int. J. Pep. Prot. Res.* 1988 31:231-238.

Hendrickson et al., "High sensitivity multianalyte immunoassay using covalent DNA-labeled antibodies and polymerase chain reaction", *Nucleic Acids Research* 1995 23(3):522-529.

Hruby V., "Conformational Restrictions of Biologically Active Peptides via Amino Acid Side Chain Groups", *Life Sci.* 1982 31:189-199.

(Continued)

*Primary Examiner*—Kenneth R. Horlick
*Assistant Examiner*—Christopher M. Babic
(74) *Attorney, Agent, or Firm*—Pepper Hamilton LLP

(57) ABSTRACT

Methods, systems and kits are provided for detecting molecules expressing a selected epitope in a sample through use of an epitope detector containing a single chain Fv for the selected epitope or a constrained epitope specific.CDR attached to an oligonucleotide.

24 Claims, No Drawings

OTHER PUBLICATIONS

Joerger et al., "Analyte Detection with DNA-Labeled Antibodies and Polymerase Chain Reaction", *Clin. Chem.* 1995 41(9):1371-1377.

Leone et al., "Molecular beacon probes combined with amplification by NASBA enable homogeneous, real-time detection of RNA", *Nucleic Acids Res.* 1998 26(9):2150-2155.

Park et al., "Rationally designed anti-HER2/neu peptide mimetic disables P185$^{HER/neu}$ tyrosine kinases in vitro and in vivo", *Nature Biotechnology* 2000 18:194-198.

In Peptides, E. Giralt and D. Andreu eds, ESCOM, Leiden, The Netherlands 1991.

Peterson & Greene, "Bacterial Expression and Characterization of Recombinant Biologically Active Anti-Tyrosine Kinase Receptor Antibody Forms", *DNA and Cell Biology* 1998 17(12):1031-1040.

Ploux O., "Cyclization of peptides on a solid support", *Int. J. Pep. Prot. Res.* 1987 29:162-169.

Prasad et al., "Contrasting Solution Conformations of Peptides Containing α,α-Dialkylated Residues with Linear and Cyclic Side Chain", *Biopolymers* 1995 35:11-20.

Qian et al., "Heterodimerization of epidermal growth factor receptor and wild-type or kinase-deficient Neu: A mechanism of interreceptor kinase activation and transphosphorylation" *Proc. Natl Acad. Sci.* 1994 91:1500-1504.

Reichmann et al., "Expression of an Antibody Fv Fragment in Myeloma Cells", *J. Mol. Biol.* 1988 203:825-828.

Romani et al., "Synthesis of the trypsin fragment 10-25/75-88 of mouse nerve growth", *Int. J. Pep. Prot. Res.* 1987 29:107-117.

Ruzicka et al., "Immuno-PCR with a Commercially Available Avidin System", *Science* 1993 260:698-699.

Sanna et al., "Rapid induction of tumor necrosis factor α in the cerebrospinal fluid after intracerebroventricular injection of lipopolysaccharide revealed by a sensitive capture immuno-PCR assay" *Proc. Natl. Acad. Sci.* 1995 92:272-275.

Schiller et al., "Synthesis of side-chain to side-chain cyclized peptide analogs on solid supports", *Int. J. Pep. Prot. Res.* 1985 25:171-177.

Sheppard et al., "Acid-labile resin linkage agents for use in solid phase peptide synthesis", *Int. J. Peptide Res.* 1982 20:451-454.

Skerra and Pluckthun, "Assembly of a Functional Immunoglobulin $F_v$ Fragment in *Escherichia coli*", *Science* 1988 240:1038-1041.

Suzuki et al., "Double Determinant Immuno-Polymearse Chain Reaction: A Sensitive Method for Detecting Circulating Antigens in Human Sera", *Jpn. J. Cancer Res.* 1995 86:885-889.

Tan et al., "Molecular Beacons:A Novel DNA Probe for Nucleic Acid and Protein Studies", *Chemistry Eur. J.* 2000 6(7)1107-1111.

Zhou et al., "Universal immuno-PCR for ultra-sensitive target protein detection", *Nucleic Acid Res.* 1993 21:6038-6039.

Deng et al., "Selection of Antibody Single-chain Variable Fragments with Improved Carbohydrate Binding by Phage Display", *J. Biol. Chem.* 1994 269:9533-9538.

Schwietzer et al., "Immunoassays with rolling circle DNA amplification:A versatile platform for ultrasensitive antigen detection", *Proc. Natl. Acad.Sci. USA* 2000 97:10113-10119.

METHOD, SYSTEMS AND KITS FOR IMMUNO-DETECTION OF EPITOPES EXPRESSED ON MOLECULES

CROSS-REFERENCE TO RELATED APPLICATIONS

This application is a continuation of Ser. No. 09/624,946 filed Jul. 25, 2000, now U.S. Pat. No. 6,743,592, which is incorporated herein by reference.

BACKGROUND OF THE INVENTION

One of the central problems in cell biology and medicine relates to the inability to monitor protein, lipids, sugars and metabolite levels and their modifications in the single living cell. A variety of technologies have been employed to improve the sensitivity of detecting these molecules.

For example, to increase the sensitivity of immunoassays able to detect proteins at very low amounts, the polymerase chain reaction (PCR) technology has been combined with conventional immuno-detection methods ((U.S. Pat. No. 5,665,539). This technology, termed immuno-PCR, provides an extremely sensitive method to detect proteins. In immuno-PCR, a linker molecule with bi-specific binding affinity for DNA and antibody is used to attach a marker DNA molecule specifically to an antigen-antibody complex, thus resulting in the formation of a specific antigen-antibody-DNA conjugate. The attached marker DNA can be amplified by PCR with the appropriate primers. As described in U.S. Pat. No. 5,665,539, antigen is immobilized on the surface of microtiter plates and subsequently detected by immuno-PCR. Using this technique, an approximately $10^5$ increase in sensitivity over an alkaline phosphatase conjugated ELISA was obtained. Sensitivity advantages of immuno-PCR have subsequently been confirmed in assays for mouse anti-lipoprotein IgG (Ruzicka et al. Science 1993 260:698-699); a human proto-oncogene protein (Zhou et al. Nucleic Acid Res. 1993 21:6038-6039); and tumor necrosis factor alpha (Sanna et al. Proc. Natl. Acad. Sci. 1995 92:272-275).

However, the original immuno-PCR protocol used a streptavidin-protein A chimera to detect the antigen-antibody complex. The variation in the affinity of protein A against different classes of IgGs limits its direct application in the detection of a broad range of antigens. Certain improved protocols tried to solve this problem by introducing biotinylated secondary antibody or free-streptavidins.

Joerger et al. (Clin. Chem. 1995 41(9): 1371-1377) demonstrated that double-stranded DNA labels can be directly attached to antibodies, thus allowing conjugate reagents to be prepared before the assay.

Suzuki et al. (Jpn. J. Cancer Res. 1995 86:885-88) describe a method called double determinant immuno-polymerase chain reaction (double-determinant immuno-PCR) which utilizes two monoclonal antibodies, in which the antigens are sandwiched, and a specific DNA molecule is used as a marker. In this method, the first monoclonal antibody to bind the circulating antigen is immobilized instead of the antigen itself. A biotinylated second monoclonal antibody is bound to the antigen and free streptavidin is used to attach a biotinylated DNA to the second monoclonal antibody. The biotinylated DNA complexed with antigen-antibody-streptavidin is amplified by PCR. The products are then analyzed by Southern blot analysis.

While these immuno-PCR techniques have provided advantages over traditional methods of protein detection such as an increase in sensitivity, there still exist several notable limitations to their use. One of the major. limitations of immuno-PCR lies in the non-linear amplification ability of PCR reaction. There is no direct correlation between the amount of signal and the amount of protein present. Thus, this technique is limited as a quantitative detection method.

U.S. Pat. No. 5,922,553 discloses a method for quantifying levels of a selected protein via a technique referred to as immuno-aRNA. In this method, a first antibody targeted to a selected protein is immobilized to a solid support. The support is then contacted with the selected protein so that the selected protein is immobilized to the first antibody. The solid support is then contacted with a RNA promoter-driven cDNA sequence covalently coupled to a second antibody targeted to the selected protein so that the second antibody binds to the bound selected protein. The amount of selected protein is determined by quantifying levels of the promoter driven cDNA sequence covalently coupled to the bound second antibody via an amplified RNA technique. In a preferred embodiment, a T7 promoter driven cDNA sequence is covalently coupled to the second antibody.

It has now been found that single chain fragments as well as exocyclic peptide based complementarity determining region (CDR) subunits can be used in this immuno-aRNA technique. Further, it has been found that PCR, as well as amplified RNA techniques, can be used to quantify the promoter driven cDNA sequence covalently coupled to the bound single chain fragment or CDR subunit. The use of smaller antibody binding units and fragments coupled with the already existing large single chain or cyclic peptide libraries and the use of robotic assistance renders this method widely useful for both medicinal and research purposes. Furthermore, a single third detector species can be coupled with double-stranded bNA and bound to either the single chain Fv or the CDRs, rendering detection uniform and simple. This is referred to herein as a universal detector.

SUMMARY OF THE INVENTION

An object of the present invention is to provide a method for detecting molecules expressing a selected epitope in a sample. In this method, an epitope anchor specific for a selected epitope is immobilized to a selected surface. The epitope anchor may comprise a single chain Fv fragment, a CDR, an antibody, or other ligand peptide or chemical or pharmaceutical that interacts with a selected epitope. The surface is then contacted with a sample suspected of containing molecules which express the selected epitope so that the molecules bind to the immobilized epitope anchor. An epitope detector comprising a single chain Fv for the selected epitope or a constrained epitope specific CDR attached to an oligonucleotide is then used to detect any bound molecules. In one embodiment, the single chain Fv or the CDR has been modified to allow for attachment of oligonucleotides to a single site. Alternatively, the method of the present invention can be performed with an epitope anchor. In this embodiment, the epitope detector is employed to define molecules bound directly to a surface.

Another object of the present invention is to provide systems for the detection of molecules expressing a selected epitope. These systems of the present invention comprise an epitope anchor specific for a selected epitope, a selected surface on which the epitope is or can be immobilized, and an epitope detector comprising a single chain Fv for the selected epitope or a constrained epitope specific CDR attached to an oligonucleotide. In one embodiment, the single chain Fv or the constrained epitope specific CDR is modified to allow for attachment of the oligonucleotides.

Yet another object of the present invention is to provide kits for the detection of molecules expressing a selected epitope which comprise an epitope anchor specific for a selected epitope and an epitope detector comprising a single chain Fv for the selected epitope or a constrained epitope specific CDR attached to an oligonucleotide. In one embodiment, the single chain Fv or the constrained epitope specific CDR is modified to allow for attachment of the oligonucleotides.

DETAILED DESCRIPTION OF THE INVENTION

The present invention relates to improved methods for quantifying levels of a selected molecule and systems and kits for performing these improved methods. In one embodiment, the method comprises binding an epitope anchor specific for a selected epitope of the molecule to a selected surface. The epitope anchor may comprise a single chain Fv fragment, a CDR, an antibody, or other ligand peptide or chemical specific for a selected epitope. In a preferred embodiment, the epitope-anchor is bound to a designated spot on the surface. For example, the surface may comprise a chip and the epitope anchor is bound to a defined spot on the chip. In one embodiment, the epitope anchor is deposited onto a surface or plate with the aid of a pipettor or similar device which permits application at a single site. The surface with the bound epitope anchor is then contacted with a sample suspected of containing molecules expressing the selected-epitope so that the molecule binds to the epitope anchor. In another embodiment, the molecule is attached to a surface directly, without the use of an epitope anchor.

Examples of samples which can be assayed via the methods of the present invention include, but are not limited to, individual cells and solutions including biological fluids such as serum. An epitope detector which can bind to any bound molecule on the surface is then used to detect and quantify the amount of bound molecule. The epitope detector comprises a single chain Fv for the selected epitope or a constrained epitope specific CDR which have been modified to allow for attachment of oligonucleotides at a single site.

Fv-fragments for selected epitopes can be produced in cells or on microorganisms by use of recombinant DNA technology. For example, Skerra and Pluckthun (Science 1988 240:1038-1044) describe an expression system for production of functional Fv fragments in *E. coli*.

A method for producing Fv fragments in eukaryotic host cells with a eukaryotic expression vector which has an operon having a DNA sequence which encodes the variable domain only of an antibody light or heavy chain has also been described (J. Mol. Biol. 1988 203:825-828). Chains of the Fv fragment are secreted and correctly assembled by the host cell such that fully functional Fv fragments are produced in the culture supernatant. In addition, the DNA coding sequence may be altered toward its 5' end so that the amino terminal end expresses a residue or residues with a surface suitable for covalent coupling of an oligonucleotide. In addition, the 3' terminal end may be varied so that cysteine residues are produced towards the C-terminal end of each variable domain permitting the variable domains in the dimer to become linked together by disulphide bonding. This may also promote assembly of the Fv fragment. Alternatively, the Fv fragment may be stabilized by use of a vector having a first DNA sequence encoding a first variable domain and a second DNA sequence encoding a second variable domain, the first and second sequences being linked by a third DNA sequence which encodes a joining peptide sequence. In this case, the joining peptide sequence is sufficiently long and flexible to allow folding of the two polypeptides into a functional single chain Fv. Preferably, the host cell is a myeloma cell line which, prior to transformation, does not secrete whole antibody or light chains. Such cells lines are well known and widely available (Reichmann et al. J. Mol. Biol. 1988 203:825-828).

It is believed that random phage technology to any hapten or chemical compound can also be used to select Fvs. (Harrison et al. United States Biochemical Pharma Ltd. (Europe), Watford, United Kingdom)

The CDR technology is well known and has been described in U.S. Pat. No. 5,334,702, U.S. Pat. No. 5,663,144, and U.S. Pat. No. 5,919,764. In general, CDRs comprises a 6 to 15 mer peptide constrained to be cyclic and modified by aromatic residues. An important step in the design of conformationally constrained peptides for use in the present invention is the delineation of the residues that are important for activity. This is generally accomplished by first synthesizing a set of analogs from the bioactive domain of the original antibody or receptor or ligand of different lengths and establishing the minimal chain lengths for the complete and partial activities. Once the minimal chain length has been established, each side chain can be systematically varied to determine the importance of charge, steric bulk, hydrophobicity, aromaticity, and chirality at each position. After evaluation of the properties of a large set of analogs, it is possible to identify the functional groups and conformation features involved in binding. Different conformationally constrained analogs can then be developed. Various means for constraining peptides have been developed.

One means involves introducing a conformationally constrained amino acid. Hruby (Life Sci. 1982 31:189-199) describes the synthesis of a large number of amino acid and dipeptide derivatives with built-in conformational constraints, as well as their incorporation into biologically active peptides. Prasad et al. (Biopolymers 1995 35:11-20) also describes a method of constraining the conformation of an amino acid unit by replacing the hydrogen atom at the α-carbon with a methyl group to produce a dialkylamino acid. U.S. Pat. No. 6,022,523 describes a method that restricts the conformational freedom of amino acids by introducing a double-bond at the C-α and C-β atoms.

Another means for constraining peptides involves introduction of covalent cross-links. Constraining the peptide backbone by introduction of covalent cross-links provides more dramatic effects than incorporating unusual amino acids. Macrocyclization is often accomplished by forming an amide bond between the peptide N- and C-termini, between a side chain and the N or C terminus, or between two side chains. A head-to-tail cyclization of side protected peptides synthesized by Fmoc/t-butyl solid phase procedures on polysterine resin derivatized with 4-hydroxymethyl-3-methoxyphenoxyacetic acid, the first generation dialkoxy-benzyl linkage agent, has been described by Sheppard, R. C. (Int. J. Peptide Res. 1982 20:451-454). In addition, the analogous linkage agent, 4-(4-hydroxymethyl-3-methoxyphenoxy)-butyric acid (HAMA), was recently employed in fragment condensation and solid phase synthesis of peptides with these highly acid sensitive linkers (In Peptides, E. Giralt and D. Andreu eds, ESCOM, Leiden, The Netherlands 1991, 131-133). The enkephalin analogs described by Schiller provide an example of side-chain to backbone covalent cyclization in which covalent attachment of the e-amino group of the D-lys residue to the C terminal backbone carboxylate group of Leu produces a cyclic 16-membered ring analog with high potency and significant μ receptor selectivity (Schiller et al. Int. J. Pep. Prot. Res. 1985; 25:171-177). BOP-reagent and carboimide/1-hydroxy-benzotriazole combinations have also been reported to be useful in the formation of cyclic peptides (Felix, A.M. Int. J. Pep. Prot. Res. 1988 31:231-238). Degrado et al. have also developed a biologically active cyclized peptide analog of the GP IIb/IIIa complex using m-aminomethylbenzoic acid as the linker (U.S. Pat. No. 6,022,523).

Disulphides can also be formed by oxidation via introduction of cysteine at certain positions. For example, Romani, S. (Int. J. Pep. Prot. Res. 1987 29:107-117) demonstrated that non-symmetrical disulphides can be built with the help of the di-tertbutyl aster of azodicarboxylic acid. Ploux, O. (Int. J. Pep. Prot. Res. 1987 29:162-169) also describes a method for formation of non-symmetrical disulphides via thiol displacement of the 3S-3-nitro-2-pyridinesulfenyl group.

In a preferred embodiment, the oligonucleotide comprises a T7 promoter driven cDNA sequence so that it can be amplified using T7 RNA polymerase. In this embodiment, double stranded cDNA is synthesized for use as a template for T7 RNA polymerase transcription. T7 RNA polymerase requires its promoter site to be double stranded.

In one embodiment, the site on the Fv or CDR to which the oligonucleotides are attached comprises a series of residues which allow the attachment of linkers consisting of chemicals such as heterodimeric coupling reagents or other linkers. These residues provide a uniform binding site for the linker attachment. The linkers attach to this site and also links oligonucleotides to the Fv or CDR. Oligonucleotides may be unmodified or modified. For example, the presence of the amplified oligonucleotide can be enhanced by incorporating a beacon or fluorescent labeled oligonucleotide into the mixture allowing for rapid semi quantitative assessment of the epitope expressing molecules (Ton et al. Chemistry 2000 6:1107-1111; Leone et al. Nucleic Acids Res. 1998 26(9):2150-2155).

Bound epitope detectors may be quantified by methods such as amplification by conventional PCR or aRNA techniques. If the detection method used is immuno aRNA, double-stranded oligonucleotides are used in the epitope detector. In this embodiment, aRNA is transcribed on the solid support using a polymerase which recognizes a specific promoter such as T7 RNA polymerase, T3 RNA polymerase or SP6 RNA polymerase, unlabeled ribonucleotides, and fluorescently labeled ribonucleotides.

A variety of means are available for detection of amplified products of the epitope detector. In one embodiment, the aRNA is detectably labeled such as with a radioactive label or a fluorescent label. Alternatively, the aRNA can be converted to cDNA and detected via methods such as gel electrophoresis, high performance liquid chromatography, hybridization assays, immunohistochemical assays and/or specific binding protein assays.

Use of Fvs and CDR peptides as the epitope detector renders this method useful in identifying larger polypeptides than can be identified by the immuno-aRNA technique of U.S. Pat. No. 5,922,553, as well as in identifying motifs in supernatants, fluids, extracts of cells or bacteria or any other eukaryotic organism. Accordingly, the method of the present invention has widespread applicability in both medicinal and research purposes. Further, the method of the present invention is more sensitive than currently available methods and provides quantitative results.

The ability of Fvs and CDR peptides to serve as epitope detectors of selected molecules in the method of the present invention was demonstrated for the p185 receptor. Using this method, the released p185 receptor was detected at a $10^8$-fold increase in sensitivity over the ELISA and about a 1000-fold increase over the Western-ECL method. For these experiments, a single chain Fv (ScFv) construct of 7.16.4 (designated as 7.16.4 ScFv) was produced in accordance with the procedure outlined by Peterson & Greene (DNA and Cell Biology 1998 17(12):1031-1040) wherein the Fv region of the heavy chain and light chain region was joined by a (gly4-Ser)5 linker. Since ScFv7.16.4 contained a polyhistidine tag, it was purified over Ni-NTA resin. After purification, the binding of 7.16.4ScFv was confirmed by FACS analysis on B104-1-1 cells, in both direct binding and competitive binding against the monoclonal antibody 7.16.4.

AHNP, a constrained exocyclic peptide designed from the CDR3.H region of the anti-human p185 antibody 4D5 was also used. AHNP binds to p185 and mimics the growth-inhibitory effects of 4D5 (Park et al. Nature Biotechnology 2000 18:194-198).

Both ScFv7.16.4 and AHNP were coupled to a double-stranded oligonucleotide (ds-oligo) to form epitope detectors. Both ds-oligo coupled 7.16.4ScFv and AHNP were able to detect their antigens, rat p185neu from B104-1-1 cells and human p185her2/neu from T6-17 cells, respectively. Further, conjugation with the ds-oligo to form the epitope detector did not change the binding affinity of the CDR detection molecules with their antigens as determined by plasmon resonance analysis. Since 7.16.4ScFv and mAb 7.16.4 have comparable binding affinity against the p185 receptor, they were used at comparable molar concentration in this assay. However, ANHP was used at a higher concentration since its affinity is lower against p185Her2/neu than 4D5.

Coupling of a ds-oligo directly to the CDR or single chain Fv can be a time-consuming procedure, particularly if the purpose is to detect hundreds or thousands of antigens in a mass screening proteomic assay. In addition, variation in the coupling efficiency can complicate the interpretation of the amplification results. Accordingly, in a preferred embodiment of the present invention, the Fv or CDR contains a general or universal epitope such as an hemagglutinin HA tag or polyhistidine tag. An example of a general or universal epitope is the poly-His-tag in the 7.16.4ScFv initially designed for the purification of the protein. A single monoclonal antibody or single chain Fv coupled with ds-DNA is then used to bind to the general epitope to create a universal epitope detector. The efficacy of a universal epitope detector in the method of the present invention was demonstrated with the poly-His-tag in the 7.16.4ScFv. In these experiments, p185 receptors were captured by AII coated on the plate, free 7.16.4ScFv was added, followed by extensive washing and then incubating with ds-oligo conjugated anti-His antibody. After T7 polymerase amplification, specific bands from lysates of $10^{-6}$ dilution of the cells were detected. Accordingly, this sensitivity was even higher than that seen with the basic protocol without a universal epitope detector.

The method of the present invention is also useful in the detection of post-translation modifications. PCR and aRNA techniques were originally developed to detect the activity of target genes at the DNA level. These methods have been adopted exclusively in the application of genomics research, sometimes combined with hybridization. Regardless of sensitivity, these methods are not able to detect the post-translation modification at the protein level. Monitoring of such events; however, is very critical since many modifications including, but not limited to, phosphorylation and glycosylation are related to the functional status of the protein. Thus, experiments were performed to demonstrate the ability of the method of the present invention to detect the phosphorylation of the p185 receptor induced by EGF treatment. A signaling model was established in which, upon EGF stimulation, EGFR heterodimerizes with and transactivates p185, resulting in the phosphorylation of tyrosine residues on the p185 receptor (Qian et al. Proc. Natl Acad. Sci. 1994 15:1500-1504). The A431 cell line, which overexpresses EGFR as well as p185 erbB2, was used in these experiments. After EGF stimulation, the p185 receptor in the cell lysate was captured by 1E1, a monoclonal antibody developed against p185erB2/neu. PY99, an IgG2b type of anti-phosphorylated Tyr antibody, was used to detect phosphorylated receptors. A second antibody, anti-IgG2b, coupled with ds-oligo, was used to probe the antigen-antibody sandwich complex. A431 cells stimulated with EGF produced a positive band, which was not observed in cells without EGF treatment. T6-17 cells, however, also showed a positive band, indicating constitutive phosphotyrosine on the p185 receptor. These data indicate that this method is capable of detecting the functional status of a protein by analyzing its modification. Epitope detectors comprising an Fv or CDR coupled to the ds-oligo can also be used to detect the functional status of the protein.

Thus, the present invention provides a sensitive detection method which eliminates concerns about the non-quantitative nature of immuno-PCR techniques and which offers vast potential in the field of proteomics. By using a polymerase which recognizes a specific promoter such as T7 RNA polymerase, T3 RNA-polymerase or SP6 RNA polymerase as well as the specific promoter in the amplification step, assays performed in accordance with this method possess linear amplification and precise quantification which are relevant to biological and medical assays. The number of factors that affect the sensitivity of detection have also been reduced. The specific binding between antigens and their Fv or monovalent CDR is the only critical parameter of this method.

The ability to provide universal epitope detectors provides the method of the present invention with multiple additional advantages. First, any cellular antigens can be detected without having been first coupled to a monoclonal antibody with ds-oligo. Without the universal probe, the method would only be useful in looking at one or several particular antigens at a time. The universal probe, on the other hand, allows for the detection of any cellular or fluid residing antigen with available Fvs or CDRs. In addition, with slight modification in the protocol, different proteins can be detected simultaneously in a single electrophoresis lane when oligonucleotides of different sizes are attached to the Fv or CDR of the epitope detector. Thus, as demonstrated herein, the method of the present invention provides a versatile technique that is applicable in the identification of protein antigens as well as post-translational modification of polypeptides and other structures such as sugars or lipids at the single cell level of detection.

It is believed that this method will also be useful in the analysis of protein interactions and the detection of small molecules. For example, ligand peptides can be used as epitope detectors on tissue samples to identify the expression of specific receptors, or verse visa. With available Fvs, CDRs, or binding proteins, small molecules such as toxins or drug metabolites, can be detected in any solution including, but not limited to, water, foods, and body fluids.

The original immuno-PCR used pure antigens in the assay. Later iterations of Immuno-PCR examined mixed antigens (Hendrickson et al. Nucleic Acids Research 1999 23(3):522-529) but only showed sensitivity of two to three orders of magnitude higher than ELISA. In a real-world assay with the background comprising a huge variety of non-specific antigens, sensitivity is always limited by the specificity of the assay. Epitopes bound by the Fvs or CDR fragments are expected to identify larger polypeptides and can be used to identify motifs in supernatants, fluids, extracts of cells or bacteria or any other eukaryotic organism. Further, actual identity of the polypeptides, organic molecules or sugar structures can be determined by computer aided analysis of data bases using the binding of several epitopes by Fvs as a guide. For example, binding by Fv a, d, e, and f would identify a sugar molecule as having side chains a, d, e, and f, and hence belonging to a family of sugars having these same side chains. In this way the present invention allows definition and identification of many, if not all molecules in a cell at any one particular time. Moreover this approach can be used to identify alternative transcriptional forms translated in an active cell or cellular supernatant. This procedure is easily amenable to 1) use with nonradioactive detection methods, 2) microtized liquid handling procedures, 3) low sample volume detection such as "protein chip" analysis and 4) robotization.

The following nonlimiting examples are provided to further illustrate the present invention.

EXAMPLES

Example 1

Materials

Antibodies used include mAbs 7.16.4 and A11, each of which is reactive with a different epitope in the extracellular domain of p185neu. The polyclonal antiserum, α-Bacneu, directed against the intracellular domain of p185neu, was used for Western Blotting. 1E1 is an IgG1 monoclonal antibody generated against the ectodomain of human p185her2/neu. rhuMAb 4D5 (Herceptin) was obtained from Genentech. The anti-phosphotyrosine monoclonal antibody PY99 was obtained from Santa Cruz Biotechnology (Santa Cruz, Calif.). The cell line B104-1-1 was derived from NIH3T3 cell by expressing rat oncogenic p185neu. The expression level of p185neu in B104-1-1 cells was determined using an $^{125}$I-labeled anti-neu mAb binding assay. NR6, negative for both EGFR and p185neu, was a subclone from NIH3T3. T6-17 was derived from NIH3T3 by over-expressing the human p185her2/neu receptor. These cell lines were all cultured in Dulbecco's Modified Eagle's medium (DMEM) containing 10% fetal bovine serum (FBS, Hyclone) at 37° C. in a 5% $CO_2$ atmosphere.

Example 2

Immunoblotting Procedures

Subconfluent cells in 10-cm dishes cells were washed twice with cold PBS and solubilized with PI/RIPA (1% Triton X-100, 1% deoxycholate, 0.1% SDS, 0.15 M NaCl, 0.01 M sodium phosphate-pH 7.4, 1% Aprotinin, 1 mM phenylmethylsulfonyl fluoride, 2 mM EDTA, 10 mM sodium pyrophosphate, 400 mM sodium orthovanadate, and 10 nM iodoacetamide buffer. Proteins were separated by proper concentration of SDS-PAGE and transferred to nitrocellulose membranes (Nitrobind, MSI). Membranes were incubated overnight with the blocking buffet (0.5% non-fat milk and 5% goat serum in PBS). For immunoblotting (Western blot) analysis, antibodies were diluted in PBS containing 0.1% non-fat milk and 1% goat serum. All polyclonal sera and secondary HRP-conjugated antibodies (Boehringer Mannheim) were used at a 1:5000 dilution. Bands were visualized using the ECL assay (Amersham).

Example 3

Expression and Purification of His-tagged 7.16.4

LB media (150 ml) containing 50 µg/ml ampicillin was inoculated with a 15 ml overnight culture of E. coli DH5 α and maintained at 30° C. until an optical density of 0.5 (600 nm) was obtained. Isopropyl-β-(-D-thiogalactopyranoside) (IPTG) was added at a final concentration of 1 mM to induce His-tagged 7.16.4ScFv. After 3 hours, cells were harvested and lysed by freezing and thawing and resuspended in 10 ml of urea lysis buffer (10 mM Tris-Cl, pH 8.0, 0.1 M $Nah_2PO_4$, 1 M NaCl, 8 M urea) supplemented with 0.5 mM phenylmethylsulfonyl fluoride, 2 µM pepstatin A, and 2 µM leupeptin. The insoluble cellular debris was removed by centrifugation (12,000×g for 15 minutes, followed by 12,000×g for 30 minutes). The clarified supernatant was mixed with 2 ml of Ni-NTA agarose followed by gentle shaking on ice for 1 hour. The mixture was loaded into an empty column and unbound protein was washed with urea lysis buffer (pH 6.3) at 4° C. His-tagged protein was eluted with urea lysis buffer (pH 4.5), and eluate fractions were examined by SDS-PAGE and FACS analysis as described in Example 4. Proteins in the peak fractions were pooled and dialyzed against TKC buffer (50 mM Tris-Cl, pH 8.0, 100 mM KCl, 10 mM $CaCl_2$, 1 mM EDTA, 0.1 mM PMSF).

Example 4

Confirmation of 7.16.4ScFv Binding by FACS Analysis

Cell-surface antigens were detected by Fluorescence-activated cell sorting (FACS). B104-1-1 cells (about $5 \times 10^5$) were incubated (30 minutes at 4° C.) in 200 µl of FACS buffer (PBS containing 0.5% bovine serum albumin and 0.02% sodium azide) containing the purified 7.16.4ScFv. Cells were then washed in FACS buffer and incubated (30 minutes, 4° C.) with anti-His antibody (Invitrogen). After this second incubation, cells were washed again in FACS buffer and further incubated with FITC-labeled IgG against mouse immunoglobulins (Sigma Chemical Co., St. Louis, Mo.). After washing with FACS buffer, the cell pellet was suspended in PBS buffer and processed for analysis by a FACS scan flow cytometer (Becton Dickinson). For each sample, 10,000 viable cells were gated following size (forward scatter, FSC) and granularity (side scatter, SSC) parameters and analyzed with CellQuest Software (Becton Dickinson). For competitive binding, B104-1-1 cells were first incubated with the monoclonal antibody 7.16.4 in the presence of different concentrations of 7.16.4ScFv. Cells were then washed in FACS buffer and further incubated with FITC-labeled IgG against mouse immunoglobulins (Sigma Chemical Co.) before analysis on the flow cytometer.

Example 5

Attachment of ds-cDNA to Antibody or Fv or CDR

A cDNA oligonucleotide of the following sequence (GAGAGAGGATCCAAGTACTAATACGACTCACTATA GGGCCGAGAGCCGAGAAGAAAGACGTTTTTTTTTT (SEQ ID NO:1)) was designed with an activatable amine at the 5' end to allow for covalent coupling to primary amines and a T7 promotor site (TAATACGACTCACTATAGGG (SEQ ID NO:2)) used to direct the synthesis of RNA from the cDNA template through the enzymatic activity of T7 RNA polymerase. For attachment of 1 µg of antibody to 30 µg of ds cDNA, or 1 µg CDR to 0.1 µg ds cDNA or 1 µg ScFv to 3 µg ds cDNA, an equal volume of 0.1% glutaraldehyde was added in 10 µl aliquots. The solution was mixed on a rotation device for 3 hours at room temperature. Ethanolamine (1 M; 1/20 volume; pH 7.5) was then added. The solution was mixed for an additional 2 hours at room temperature. The protein-DNA complex was stored at 4° C.

Example 6

RNA amplification

RNA amplification was performed in 96-well plates containing the first Ab-Antigen complex. The following reagents were added: 1× RNA amplification buffer (40 mM Tris-base, pH 7.5, 7 mM $MgCl_2$, 10 mM NaCl, 2 mM Spermidine; 5 mM DTT; 250 µM ATP, UTP, GTP; 5 µM CTP; 0.5 µl RNAsin; 1000 U T7 RNA Polymerase and 3 µl $P^{32}$-CTP. The solution was then incubated for 4 hours at 37° C. The RNA product was removed from the wells and 3 µl was added to 3 µl of reaction stop solution (95% formamide, 10 mM EDTA, 0.1% bromophenol blue, 0.1% xylene cyanol) and electrophoresed on a 15% denaturing polyacrylamide gel. The gel was apposed to a phosphoimager screen for 5-60 minutes and developed on a phosphoimager at 100 uM resolution.

Example 7

Standard Sandwich ELISA as a Control Method

Ninety-six well microtiter plates (Nunc-Immuno Plate, MaxiSorpTM) were coated with the 1E1 (a monoclonal antibody directed against the extracellular domain of human p185) by incubating plates overnight at 40° C. with 100 µl of coating buffer (antibody concentration: 5 µg/ml). Plates were then washed three times with PBS containing 0.2% TWEEN 20 (PBS-T; 200 µl/well), blocked with PBS containing 0.5% FBS and 0.2% TWEEN 20 (200 µl/well) for 1 hour at room temperature, and washed again three times with PBS-T (200 µl/well). In parallel, 100 Al of a serial dilution of T6-17 cell lysates were added to the plate and incubated for 2 hours at room temperature. After this incubation step, plates were washed with PBS-T (six times, 200 µ/well) and incubated with humanized anti-p185Her2 antibody 4D5 (150 ng/ml, 50 µl/well) for 2 hours at room temperature. Subsequently, plates were washed six times and incubated with 50 µl of anti-human IgG-HRP (Zymed; final dilution: 1:10,000) for another 2 hours at room temperature. Enzymatic reactions were carried out at room temperature by adding TMB (2.5 mM each in 0.1 M phosphate-citrate buffer, pH 5.0) (100 µl of each reagent/well). Reactions were stopped after 15-60 minutes by the addition of 50 µl of 1 M $H_2SO_4$. Color development was measured at 450 nm using the ELISA reader.

What is claimed is:

1. A method for detecting molecules expressing a selected epitope in a sample comprising:
   a) immobilizing a molecule expressing a selected epitope in a sample to a selected surface;
   b) contacting the surface with an epitope detector that binds to the selected epitope so that the epitope detector binds to immobilized molecules on the surface which comprise the selected epitope, wherein the epitope detector
      i) is selected from the group consisting of: a single chain Fv for the selected epitope and a constrained epitope selected specific CDR, and
      ii) has an oligonucleotide attached to it, said oligonucleotide comprises an RNA promoter linked to a nucleotide sequence that is a template for an RNA transcript;
   c) producing an amplified RNA product by RNA amplification using the oligonucleotide as a substrate, and
   d) detecting any epitope detector bound to the surface by detecting amplified RNA product, wherein bound epitope detector is indicative of molecules expressing the selected epitope in the sample.

2. The method of claim 1 wherein the molecule expressing a selected epitope is immobilized to the selected surface via binding to an epitope anchor on the surface which is specific for the selected epitope.

3. The method of claim 1 wherein the molecule expressing a selected epitope is post-translationally modified.

4. The method of claim 1 where the selected surface is a chip or a well of a plate.

5. The method of claim 1 wherein the oligonucleotide is a double stranded cDNA molecule.

6. The method of claim 1 wherein the oligonucleotide comprises an RNA promoter selected from the group consisting of: a T7 RNA promoter, a T3 RNA promoter and an SP6 RNA promoter.

7. The method of claim 1 wherein the amount of molecules expressing the selected epitope in the sample is quantified by quantifying the amount of epitope detector bound to the surface, wherein the amount of epitope detector bound to the surface is determined by quantifying the amount of amplified RNA product.

8. The method of claim 7 where the selected surface is a chip or a well of a plate.

9. The method of claim 7 wherein the oligonucleotide is a double stranded cDNA molecule.

10. The method of claim 7 wherein the oligonucleotide comprises an RNA promoter selected from the group consisting of: a T7 RNA promoter, a T3 RNA promoter and an SP6 RNA promoter.

11. A method for detecting molecules expressing a selected epitope in a sample comprising:
   a) immobilizing a molecule expressing a selected epitope in a sample to a selected surface;
   b) contacting the surface with an epitope detector that binds to the selected epitope so that the epitope detector binds to immobilized molecules on the surface which comprise the selected epitope, wherein the epitope detector
      i) is selected from the group consisting of: a single chain Fv for the selected epitope and a constrained selected epitope specific CDR, and
      ii) comprises a general epitope;
   c) contacting said epitope detector with a universal epitope detector that binds to the general epitope so that the universal epitope detector binds to the epitope detector that is bound on the surface to an immobilized molecule which comprise the selected epitope, wherein the universal epitope detector has an oligonucleotide attached thereto, said oligonucleotide comprising an RNA promoter linked to a nucleotide sequence that is a template for an RNA transcript;
   d) producing an amplified RNA product by RNA amplification using the oligonucleotide as a substrate, and e) detecting any epitope detector bound to the surface by detecting amplified RNA product, wherein bound epitope detector is indicative of molecules expressing the selected epitope in the sample.

12. The method of claim 11 wherein the molecule expressing a selected epitope is immobilized to the selected surface via binding to an epitope anchor on the surface which is specific for the selected epitope.

13. The method of claim 11 wherein the molecule expressing a selected epitope is post-translationally modified.

14. The method of claim 11 where the selected surface is a chip or a well of a plate.

15. The method of claim 11 wherein the oligonucleotide is a double stranded cDNA molecule.

16. The method of claim 11 wherein the oligonucleotide comprises an RNA promoter selected from the group consisting of: a T7 RNA promoter, a T3 RNA promoter and an SP6 RNA promoter.

17. The method of claim 11 wherein the amount of molecules expressing the selected epitope in the sample is quantified by quantifying the amount of epitope detector bound to the surface, wherein the amount of epitope detector bound to the surface is determined by quantifying the amount of amplified RNA product.

18. The method of claim 17 where the selected surface is a chip or a well of a plate.

19. The method of claim 17 wherein the oligonucleotide is a double stranded cDNA molecule.

20. The method of claim 17 wherein the oligonucleotide comprises an RNA promoter selected from the group consisting of: a T7 RNA promoter, a T3 RNA promoter and an SP6 RNA promoter.

21. The method of claim 1 wherein the molecules expressing a selected epitope are protein molecules.

22. The method of claim 7 wherein the molecules expressing a selected epitope are protein molecules.

23. The method of claim 11 wherein the molecules expressing a selected epitope are protein molecules.

24. The method of claim 17 wherein the molecules expressing a selected epitope are protein molecules.

* * * * *

UNITED STATES PATENT AND TRADEMARK OFFICE
CERTIFICATE OF CORRECTION

PATENT NO. : 7,361,464 B2
APPLICATION NO. : 10/856057
DATED : April 22, 2008
INVENTOR(S) : Mark E. Greene et al.

It is certified that error appears in the above-identified patent and that said Letters Patent is hereby corrected as shown below:

On the Title Page,
Item (56) References Cited:
OTHER PUBLICATIONS
Please insert missing reference -- Harrison et al., United States Biochemical Pharma Ltd. (Europe) Watford, United Kingdom --.
Page 2, "Park et al.," reference, delete "$P185^{HER/neu}$" and insert -- $P185^{HER2/neu}$ --.
Page 2, "Prasad et al.," reference, delete "Chain"," and insert -- Chains", --.

Column 2,
Line 2, after "major" delete ".".
Line 34, delete "bNA" and insert -- DNA --.

Column 3,
Line 24, delete "epitope-anchor" and insert -- epitope anchor --.
Line 44, delete "Fv-fragments" and insert -- Fv fragments --.

Column 7,
Line 1, delete "events;" and insert -- events, --.

Column 9,
Line 2, delete "buffet" and insert -- buffer --.
Line 23, delete "$Nah_2PO_4$," and insert -- $NaH_2PO_4$, --.

UNITED STATES PATENT AND TRADEMARK OFFICE
CERTIFICATE OF CORRECTION

PATENT NO. : 7,361,464 B2
APPLICATION NO. : 10/856057
DATED : April 22, 2008
INVENTOR(S) : Mark E. Greene et al.

It is certified that error appears in the above-identified patent and that said Letters Patent is hereby corrected as shown below:

Column 10,
Line 47, delete "40° C." and insert -- 4° C. --.
Line 53, delete "100 Al" and insert -- 100 µl --.
Lines 56-57, delete "200 µ/well)" and insert -- 200 µl/well) --.

Signed and Sealed this

Ninth Day of June, 2009

JOHN DOLL
*Acting Director of the United States Patent and Trademark Office*

SEQUENCE LISTING

<160> NUMBER OF SEQ ID NOS: 2

<210> SEQ ID NO 1
<211> LENGTH: 70
<212> TYPE: DNA
<213> ORGANISM: Artificial Sequence
<220> FEATURE:
<223> OTHER INFORMATION: synthetic oligonucleotide

<400> SEQUENCE: 1

```
gagagaggat ccaagtacta atacgactca ctatagggcc gagagccgag aagaaagacg      60
tttttttttt                                                            70
```

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2

```
taatacgact cactataggg                                                 20
```